(12) United States Patent
Goebel et al.

(10) Patent No.: US 8,288,713 B2
(45) Date of Patent: Oct. 16, 2012

(54) LASER MULTI-SENSOR SYSTEM FOR THE SELECTIVE TRACE ANALYSIS OF ORGANIC MATERIALS

(75) Inventors: Johann Goebel, Munich (DE); Peter Peuser, Riemerling (DE)

(73) Assignee: EADS Deutschland GmbH, Ottobrunn (DE)

( * ) Notice: Subject to any disclaimer, the term of this patent is extended or adjusted under 35 U.S.C. 154(b) by 177 days.

(21) Appl. No.: 12/744,815

(22) PCT Filed: Nov. 20, 2008

(86) PCT No.: PCT/EP2008/009814
§ 371 (c)(1),
(2), (4) Date: Oct. 21, 2010

(87) PCT Pub. No.: WO2009/068218
PCT Pub. Date: Jun. 4, 2009

(65) Prior Publication Data
US 2011/0031393 A1     Feb. 10, 2011

(30) Foreign Application Priority Data
Nov. 27, 2007   (DE) .................. 10 2007 057 374

(51) Int. Cl.
*H01J 49/00*     (2006.01)

(52) U.S. Cl. ........................ 250/281; 250/286

(58) Field of Classification Search ........... 250/281, 250/282, 286, 285
See application file for complete search history.

(56) References Cited

U.S. PATENT DOCUMENTS

| | | | |
|---|---|---|---|
| 7,807,963 B1 * | 10/2010 | Bier | 250/283 |
| 2004/0057050 A1 | 3/2004 | Beck et al. | |
| 2005/0130317 A1 * | 6/2005 | Ventzki et al. | 436/177 |

FOREIGN PATENT DOCUMENTS

| | | |
|---|---|---|
| DE | 102 47 272 A1 | 4/2004 |
| DE | 103 06 900 A1 | 9/2004 |
| JP | 60-66155 A | 4/1985 |
| WO | WO 2007/123555 A2 | 11/2007 |
| WO | WO 2009/016169 A2 | 2/2009 |

OTHER PUBLICATIONS

Joerg Hermann, et al., "Analyses of Gas-Phase Reactions during Pulsed-Laser Ablation using Laser-induced Fluorescence-, Absorption- and Emission- Spectroscopy", Proceedings of the SPIE—The International Society for Optical Enigneering SPIE-Int., 2002, pp. 27-40, vol. 4762, USA, XP002517925.

(Continued)

*Primary Examiner* — Kiet T Nguyen
(74) *Attorney, Agent, or Firm* — Crowell & Moring LLP

(57) ABSTRACT

The invention relates to a multi-sensor laser system for the selective trace analysis of organic material, the multi-sensor system having at least one laser ion mobility spectrometer, an absorption spectrometer and a fluorescent measuring device. The system is characterized in that it is equipped with a device for the simultaneous generation of a common laser beam with different wavelengths and pulses for the simultaneous operation of the laser ion mobility spectrometer, the absorption spectrometer and the fluorescent measuring device. This avoids the disadvantages of the known solutions in prior art and provides an improved solution for the highly sensitive and highly selective trace analysis of organic material, in particular hazardous substances such as explosives and warfare agents in the air.

10 Claims, 2 Drawing Sheets

OTHER PUBLICATIONS

F. Ames, et al., "A High-Temperature Laser Ion Source for Trace Analysis and Other Applications", Applied Physics B: Photophysics and Laser Chemistry, Sep. 1, 1990, pp. 200-206, No. 3, Berlin, Germany, XP000149684.

E. Sani, et al., "General Purpose Plasma Catalysis Pilot Plant for Gaseous Pollutants Removal: Diagnostic and Control System", Proceedings of the Eleventh International Conference on Gas Discharges and Their Applications, Sep. 11-15, 1995pp. 430-433, vol. 2, Tokyo, Japan, XP008103191.

International Search Report including partial translation dated Apr. 21, 2009 Six (6) pages.

* cited by examiner

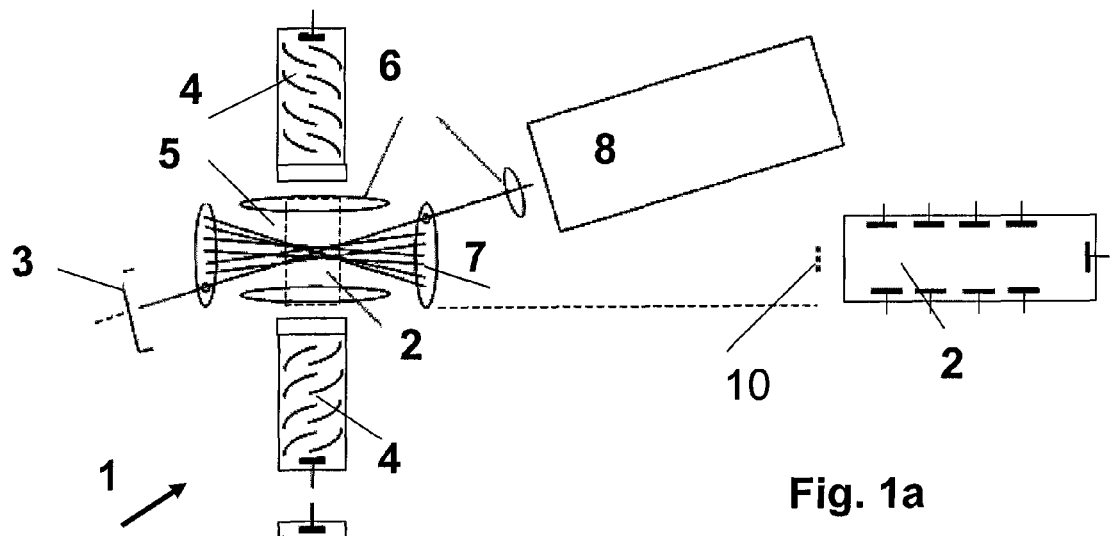
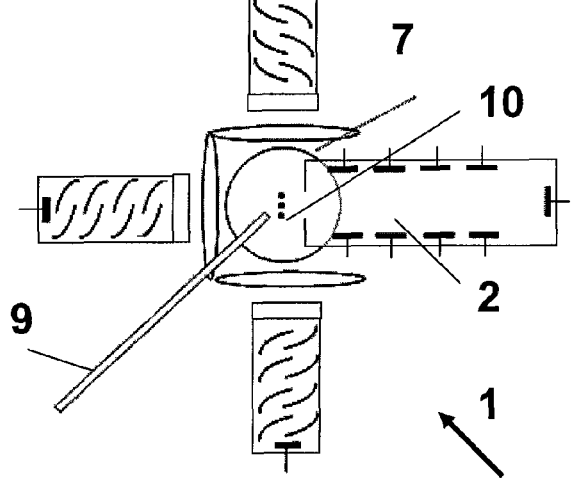
Fig. 1a
Fig. 1b

LASER MULTI-SENSOR SYSTEM FOR THE SELECTIVE TRACE ANALYSIS OF ORGANIC MATERIALS

BACKGROUND AND SUMMARY OF THE INVENTION

The present invention relates to a laser multi-sensor system for the selective trace analysis of organic materials, wherein the laser multi-sensor system has at least one laser ion mobility spectrometer, an absorption spectrometer and a fluorescence measuring device.

Apparatuses for detecting individual organic materials are known from the prior art. These known apparatuses generally have a closed sample chamber for analyzing the materials. The analysis itself takes a few minutes in such apparatuses from the prior art.

Apparatuses for detecting bacteria, viruses or other microparticles provide for example for the filtering out and marking of the corresponding particles before these can then be detected automatically.

Thus, DE 103 06 900 A1 describes a spectrometer with a laser arrangement for analyzing gases. Therein, the spectrometer comprises a chamber for holding a gas, a device for generating a potential drop in the chamber, a laser-light source and an optical resonator formed by opposing mirrors or designed as a ring resonator. A laser beam for ionizing the gas is generated within the chamber. Here, an ion collector is used to detect the accelerated ions.

A similar apparatus is described in DE 102 47 272 A1, in which, however, a multi-reflection cell is provided instead of an optical resonator made from opposing mirrors, which multi-reflection cell has mirrors designed such that the laser beam is many-times reflected between the mirrors. This increases the path length of the laser beam interacting with the gas, which leads to a higher current at the ion collector.

The optical arrangement generated by means of the mirrors forms a multiplicity of laser beams respectively running between two reflection points, which laser beams intersect in a central region and fan out toward the mirrors.

A disadvantage of the known prior art is that generally only one of many hazardous-material classes are covered by the respective apparatuses. Examining a sample in respect of a plurality of organic materials therefore generally has to be carried out sequentially, which is problematic, particularly in the case of small samples. It is also possible for the sequentially performed analyses to lead to changes in the sample, which falsify the measurement result. In general, this cannot ensure that the relevant information originates from one and the same molecule ensemble.

Furthermore, the known apparatuses are not able to detect the materials directly from the surrounding air without pre-enrichment. The usual sampling times of the order of minutes cannot be applied to certain applications, such as checkpoints, gate monitoring, danger monitoring, etc. Moreover, the known solutions are often heavy and bulky and are associated with high acquisition costs.

Therefore, the invention is based on the object of avoiding the disadvantages of the known solutions from the prior art and providing an improved solution for highly sensitive and highly selective trace analysis of organic materials, in particular hazardous materials such as explosive materials and warfare agents, in the air. More particularly, these materials should be recognized and verified in the surrounding air in a quick and accurate fashion.

According to the invention, this object is achieved by a laser multi-sensor system for the selective trace analysis of organic materials with the features of patent claim 1. Advantageous refinements and developments of the invention are specified in the dependent claims.

The laser multi-sensor system according to the invention for the selective trace analysis of organic materials is characterized in that provision is made for an apparatus for simultaneously generating a common laser beam with differing wavelengths and pulses for simultaneously operating the laser ion mobility spectrometer, the absorption spectrometer and the fluorescence measuring device. This establishes a compact integrated laser-based multi-sensor system for examining one and the same sample by simultaneous measurements using a detection system consisting of an arrangement that integrates a laser ion mobility spectrometer (LIMS), an absorption spectrometer and a fluorescence measuring device in a special, compact configuration. As a result of the simultaneous examination of a sample by means of various physical laser measuring methods, which convey differing physical information about the sample, a significant increase is achieved in the selectivity and sensitivity with respect to the detection of explosive and hazardous materials.

This avoids the disadvantages of the known solutions from the prior art, and provides an improved solution for the highly-sensitive and highly-selective trace analysis of organic materials, in particular hazardous materials such as explosive materials and warfare agents, in the air. More particularly, these materials are recognized and verified in the surrounding air in a quick and accurate fashion. Further advantages over other methods are a significant improvement in the significance of detection methods for explosive materials and hazardous materials, a significant improvement in sensitivity and selectivity and a high mobility of the laser multi-sensor system according to the invention as a result of a compact sensor system.

An advantageous development of the invention provides for the apparatus for generating a common laser beam to be provided with wavelengths in the IR, visible and UV range.

An advantageous development of the invention provides for a planar multi-reflection configuration to be provided for the absorption measurement. As a result of the long beam path, a large number of reflection signals perpendicular to the laser beam are generated.

An advantageous development of the invention provides for the laser ion mobility spectrometer to be provided for the multiple passage of the sample through the laser radiation. One of the measurement principles of the present invention is based on spectroscopic gas-sensor technology, which operates using the velocity of ions during the movement thereof under the influence of an electric drift-field in the air. Due to the differing mass and due to the differing cross section of the ions, a distinction between individual materials can easily be achieved.

The signal is measured as an arrival-time spectrum of various ion types, like in time-of-flight spectroscopy, but without the requirement of bulky instrumentation, vacuum pumps, etc.

So-called ion mobility spectroscopy (IMS) is proposed for the present invention. Most instruments used in this case operate with a membrane inlet system and radioactive ion sources. This protects the instruments from water, vapor and all possible other contaminants in the air. This ionization principle is based on a charge transfer reaction mechanism, also referred to as chemical ionization.

An important element of the invention is the combination of a very sensitive ion-detection apparatus with a highly selective, laser-based ionization mechanism.

The ionization process itself is a multi-photon ionization step leading to a more detailed ion spectrum, allowing a better selectivity of the ionization stage and a better sensitivity down into the ppt (parts per trillion) range.

The analysis part of the ion mobility spectroscopy instrumentation is used for detecting, for example, enzymatic reaction products, pyrolysis starting materials of bio-molecules or chemicals from toxins.

An advantageous development of the invention provides for the fluorescence measuring device to have a large solid angle for detecting characteristic fluorescence radiations. The fluorescence device is also suitable for detecting bio-molecules, for example.

A particularly advantageous development of the invention provides for the laser multi-sensor system to be provided for simultaneously measuring a sample using the laser ion mobility spectrometer, the absorption spectrometer and the fluorescence measuring device. It is an important feature of the invention that the measurements are performed simultaneously and the laser excitation takes place in a single laser beam because only this ensures that the relevant information originates from one and the same molecule ensemble. Only this affords the possibility of obtaining a plurality of items of information by a single sample and of improving the significance.

An advantageous development of the invention provides for the simultaneous measurement to take place in real time. This makes the laser multi-sensor system according to the invention outstandingly suitable for the use at security gates, for example for the identity checkpoints at airports.

An advantageous development of the invention provides for the apparatus for simultaneously generating a common laser beam to be provided as a laser system, which has at least three laser sources with differing wavelengths that are coupled into a common beam by means of a beam coupler. By way of example, it is possible to use a compact laser unit that simultaneously generates suitable radiation at the optimum wavelengths for the respective detection methods and pulses in the IR, visible and UV range.

Another advantageous development of the invention provides for the laser system to have a pulse control unit for synchronizing the at least three laser sources of differing wavelength. As a result of this, the laser beams with differing wavelengths are identically clocked. All three lasers are synchronized by the common pulse control unit such that the radiation is emitted in a single pulse. The long component contains the radiation for the absorption and fluorescence measurement, and the short component brings about the ionization of the sample molecules. In terms of timing, the short pulse component is preferably at the end of the long component, since the ions are then suctioned away by the electric field in the ion mobility spectrometer and wander to the detection electrode.

Finally, an advantageous development of the invention provides for provision to be made for an evaluation unit for interpreting the detector signals. By way of example, the detector signals are interpreted with the aid of optimized pattern recognition methods.

Further measures improving the invention are explained in more detail below together with the description of a preferred exemplary embodiment of the invention on the basis of the figures, in which

BRIEF DESCRIPTION OF THE DRAWING FIGURES

FIG. 1a shows a schematic illustration of a measurement arrangement according to the present invention;

FIG. 1b shows a view of the measurement arrangement from FIG. 1a, rotated by 90°;

DETAILED DESCRIPTION OF THE INVENTION

Figure 2:
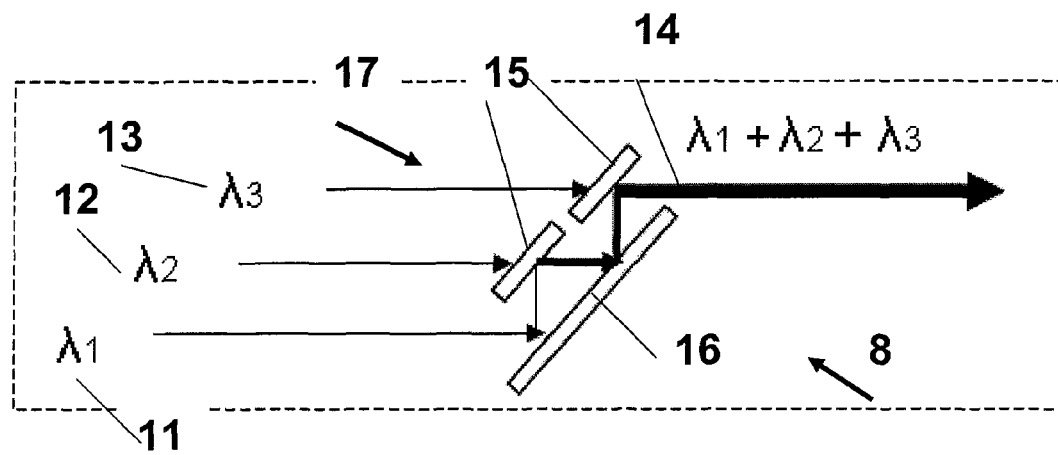
FIG. 2 shows a schematic illustration of the beam coupler of a laser system according to the invention in a side view.

FIG. 1a shows a schematic sketch of the principle of the measurement arrangement. FIG. 1b shows the measurement arrangement from FIG. 1a, rotated by 90°. The preferred embodiment of a laser multi-sensor system 1 according to the invention illustrated in FIGS. 1a and 1b allows a long measurement path for the absorption measurement by means of a detector for absorption measurement 3, for example using IR radiation, through a planar multi-reflection cell 5. Here, the multi-reflection cell 5 has oppositely arranged mirrors 7 and optical lenses 6.

Furthermore, a large ionization yield for a coupled laser ion mobility spectrometer 2 is made possible, which is achieved by the multiple passage of the laser radiation, preferably UV radiation, through the sample 10. In FIG. 1a, the laser ion mobility spectrometer 2 (LIMS) is arranged perpendicular to the plane of the drawing, which is why it has been pivoted out to the right edge of the drawing for visualization reasons.

Moreover, the laser multi-sensor system 1 according to the invention affords a large solid angle for the detection of characteristic fluorescence radiation by means of a fluorescence detector 4. In the process, the fluorescence radiation is excited by means of an additional wavelength contained in the measurement beam. Finally, the system 1 according to the invention allows simultaneous analysis of a sample 10 using all three aforementioned methods, i.e. laser ion mobility spectroscopy, absorption spectroscopy and fluorescence analysis.

By way of example, a sample 10 can be contained in a gas flow guided into the center of the measurement arrangement by means of a sample inlet 9 formed by, for example, a tube with preferably a small diameter. It is also possible to insert a sample 10, which is situated on a suitable small carrier, into the measurement center, where, for example, said sample is evaporated from the carrier by heating.

FIG. 2 shows a schematic illustration of the beam coupler 17, or of the optical interface, of a laser system 8, as is used in a laser multi-sensor system according to the invention. The laser system 8 has a first laser source 11, a second laser source 12 and a third laser source 13, which are designed as solid-state lasers in the present exemplary embodiment and the laser beams of which propagate collinearly. The laser beams with the wavelengths $\lambda_1$, $\lambda_2$ and $\lambda_3$ are optimally matched to the various detection methods and are provided in a common laser beam 14 by means of a beam coupler 17. In the present exemplary embodiment, the beam coupler 17 consists of two edge filters 15 and a mirror 16, by means of which the laser beams of the laser sources 11, 12, 13 are deflected and superposed.

Figure 3:
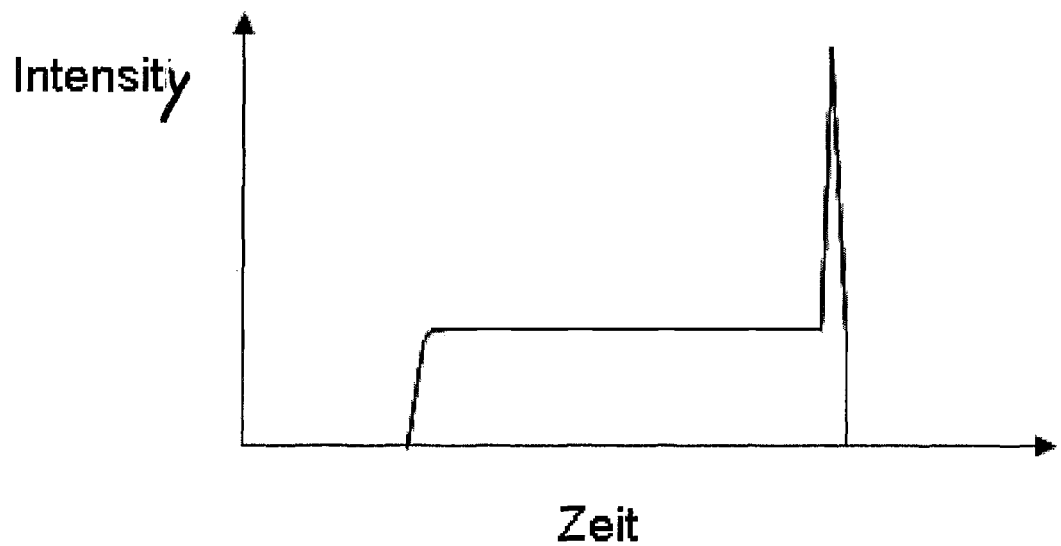
FIG. 3 shows a schematic illustration of the synchronized laser pulses.

FIG. 3 shows a schematic illustration of a synchronized laser pulse. All three lasers are synchronized by means of a common pulse control unit (not illustrated) such that the radiation is emitted in a single pulse. In doing so, the pulse contains a long component of the order of approximately 1 μs, up to a few ms and a short component of the order of a few ns, as is explained by FIG. 3. The long component contains the radiation for the absorption and fluorescence measurement and the short component brings about the ionization of the sample molecules. In terms of timing, the short pulse component is at the end of the long component, since the ions are then suctioned away by the electric field in the ion mobility spectrometer and wander to the detection electrode. This temporal succession, i.e. triggering the peak for the ionization at the end of the measurement, prevents an adverse influence on the fluorescence measurement and the absorption measurement and the obtained measurement values have not been falsified.

The embodiment of the invention is not restricted to the aforementioned preferred exemplary embodiment. Rather, a number of variants are feasible that make use of the solution claimed in the patent claims, even in the case of differently designed embodiments.

LIST OF REFERENCE SIGNS

1 Laser multi-sensor system
2 Laser ion mobility spectrometer
3 Detector for adsorption measurement
4 Fluorescence detector
5 Multi-reflection cell
6 Optical lens
7 Mirror
8 Laser system
9 Sample inlet
10 Sample
11 Laser source 1
12 Laser source 2
13 Laser source 3
14 Common laser beam
15 Edge filter
16 Mirror

The invention claimed is:

1. A laser multi-sensor system for the selective trace analysis of organic materials, wherein the multi-sensor system comprises:
at least one laser ion mobility spectrometer,
an absorption spectrometer,
a fluorescence measuring device, and
an apparatus for simultaneously generating a common laser beam with differing wavelengths and pulses for simultaneously operating the laser ion mobility spectrometer, the absorption spectrometer and the fluorescence measuring device.

2. The laser multi-sensor system as claimed in claim 1, wherein the apparatus for generating a common laser beam is provided with wavelengths in the IR, visible and UV range.

3. The laser multi-sensor system as claimed in claim 1, wherein a planar multi-reflection configuration is provided for the absorption spectrometer.

4. The laser multi-sensor system as claimed in claim 1, wherein the laser ion mobility spectrometer is provided for the multiple passage of a sample through the laser radiation.

5. The laser multi-sensor system as claimed in claim 1, wherein the fluorescence measuring device has a large solid angle for detecting characteristic fluorescence radiations.

6. The laser multi-sensor system as claimed in claim 1, wherein the laser multi-sensor system is provided for simultaneously analyzing a sample using the laser ion mobility spectrometer, the absorption spectrometer and the fluorescence measuring device.

7. The laser multi-sensor system as claimed in claim 1, wherein the simultaneous analysis takes place in real time.

8. The laser multi-sensor system as claimed in claim 1, wherein the apparatus for simultaneously generating a common laser beam is provided as a laser system, which has at least three laser sources of differing wavelength that are coupled into a common beam by means of a beam coupler.

9. The laser multi-sensor system as claimed in claim 8, wherein the laser system has a pulse control unit for synchronizing the at least three laser sources of differing wavelength.

10. The laser multi-sensor system as claimed in claim 1, wherein an evaluation unit for interpreting a detector signal.

* * * * *